United States Patent
Campbell et al.

(10) Patent No.: US 6,258,089 B1
(45) Date of Patent: Jul. 10, 2001

(54) ANTERIOR CERVICAL PLATE AND FIXATION SYSTEM

(75) Inventors: Christopher M. Campbell; Donald E. Anselm, both of Bermuda Dunes; Jason D. Blain, Palm Desert; Joel P. Bales, Palm Desert; Dan L. Pastrick, Palm Desert; George A. Ramirez, San Jacinto; Rick B. Delamarter, Los Angeles, all of CA (US); Leonard J. Tokish, Jr., Issaquah, WA (US)

(73) Assignee: Alphatec Manufacturing, Inc., Palm Desert, CA (US)

( * ) Notice: Subject to any disclaimer, the term of this patent is extended or adjusted under 35 U.S.C. 154(b) by 0 days.

(21) Appl. No.: 09/314,617

(22) Filed: May 19, 1999

Related U.S. Application Data

(60) Provisional application No. 60/085,962, filed on May 19, 1998, and provisional application No. 60/105,976, filed on Oct. 28, 1998.

(51) Int. Cl.[7] ............................. A61B 17/68; A61B 17/70
(52) U.S. Cl. ................................................ 606/61; 606/60
(58) Field of Search .................... 623/16, 17; 606/60, 606/61, 69, 72, 73

(56) References Cited

U.S. PATENT DOCUMENTS

| | | | |
|---|---|---|---|
| 5,176,678 | * | 1/1993 | Tsou ........................................ 606/61 |
| 5,234,430 | * | 8/1993 | Huebner ................................ 606/60 |
| 5,261,910 | * | 11/1993 | Warden et al. ...................... 606/61 |
| 5,330,473 | * | 7/1994 | Howland ............................... 606/61 |
| 5,454,811 | * | 10/1995 | Huebner ................................ 606/60 |
| 5,486,176 | * | 1/1996 | Hildebrand et al. ................. 606/71 |
| 5,498,263 | * | 3/1996 | DiNello et al. ....................... 606/61 |
| 5,549,608 | * | 8/1996 | Errico et al. ........................... 606/61 |
| 5,554,157 | * | 9/1996 | Errico et al. ........................... 606/61 |
| 5,584,834 | * | 12/1996 | Errico et al. ........................... 606/61 |
| 5,643,265 | * | 7/1997 | Errico et al. ........................... 606/70 |
| 5,647,873 | * | 7/1997 | Errico et al. ........................... 606/61 |
| 5,662,652 | * | 9/1997 | Schafer et al. ........................ 606/61 |
| 5,667,506 | * | 9/1997 | Sutterlin ................................. 606/61 |
| 5,669,911 | * | 9/1997 | Errico et al. ........................... 606/61 |
| 5,672,175 | * | 9/1997 | Martin .................................... 606/61 |
| 5,676,666 | * | 10/1997 | Oxland et al. ........................ 606/61 |
| 5,690,630 | * | 11/1997 | Errico et al. ........................... 606/61 |
| 5,713,900 | * | 2/1998 | Benzel et al. ......................... 606/61 |
| 5,725,528 | * | 3/1998 | Errico et al. ........................... 606/61 |
| 5,733,285 | * | 3/1998 | Errico et al. ........................... 606/61 |
| 5,733,286 | * | 3/1998 | Errico et al. ........................... 606/61 |
| 5,735,851 | * | 4/1998 | Errico et al. ........................... 606/61 |

(List continued on next page.)

\* cited by examiner

*Primary Examiner*—Paul J. Hirsch
*Assistant Examiner*—Michael B. Priddy
(74) *Attorney, Agent, or Firm*—Larkin, Hoffman, Daly & Lindgren, Ltd.; Frederick W. Niebuhr, Esq.

(57) ABSTRACT

An anterior cervical plate is disclosed, along with threaded fasteners for securing the plate to vertebrae or other osseous material. The cervical plate has several pockets or apertures, preferably at least four, to receive a corresponding number of the fasteners. The pockets have spherical surfaces, and the fasteners have heads with similarly sized spherical surfaces, which when engaged permit each of the fasteners to be oriented at a variety of projection angles with respect to the plate. In connection with each pocket, the cervical plate incorporates a fastener retaining feature. The feature can take the form of a cantilevered tab or a beam supported at its opposite ends, in each case plastically deformable between an open position for admitting the fastener and a closed position for preventing retraction.

41 Claims, 8 Drawing Sheets

U.S. PATENT DOCUMENTS

| | | | |
|---|---|---|---|
| 5,776,135 * | 7/1998 | Errico et al. | 606/61 |
| 5,785,711 * | 7/1998 | Errico et al. | 606/61 |
| 5,797,911 * | 8/1998 | Sherman et al. | 606/61 |
| 5,800,435 * | 9/1998 | Errico et al. | 606/61 |
| 5,810,819 * | 9/1998 | Errico et al. | 606/61 |
| 5,817,094 * | 10/1998 | Errico et al. | 606/61 |
| 5,876,402 * | 3/1999 | Errico et al. | 606/61 |
| 5,879,350 * | 3/1999 | Sherman et al. | 606/61 |
| 5,885,286 * | 3/1999 | Sherman et al. | 606/61 |
| 5,891,145 * | 4/1999 | Morrison et al. | 606/61 |
| 5,899,901 * | 5/1999 | Middleton | 606/61 |
| 5,904,683 * | 5/1999 | Pohndorf et al. | 606/61 |
| 5,954,725 * | 9/1999 | Sherman et al. | 606/78 |
| 5,964,760 * | 10/1999 | Richelsoph | 606/61 |
| 5,976,136 * | 11/1999 | Bailey et al. | 606/61 |

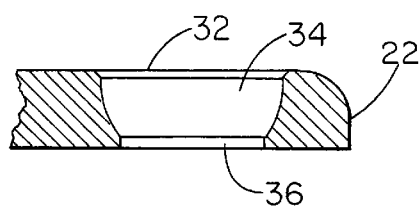
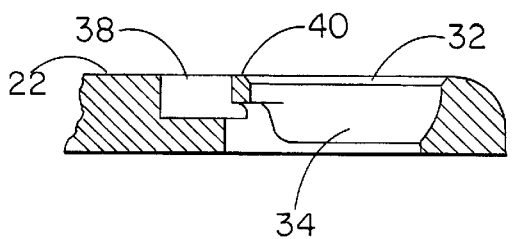
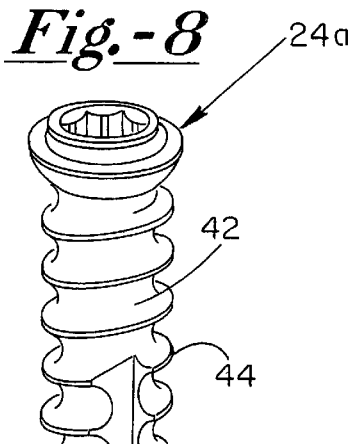
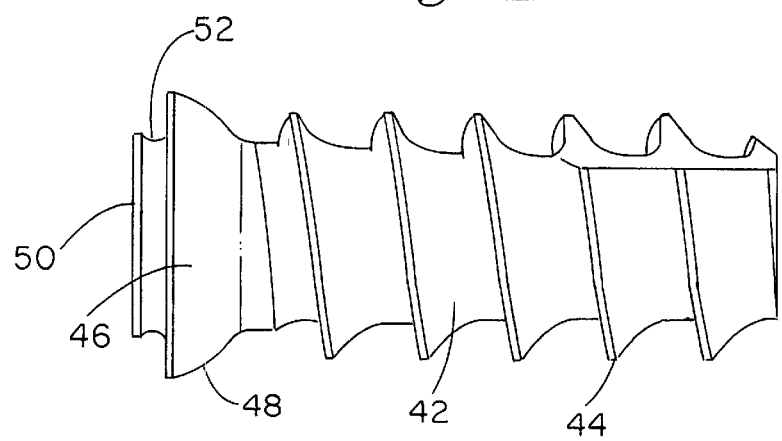
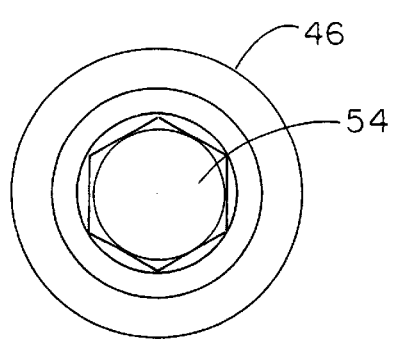
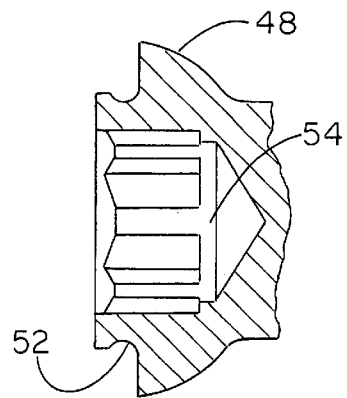

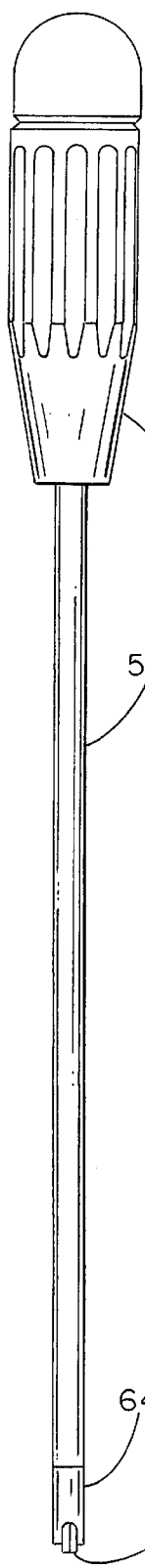
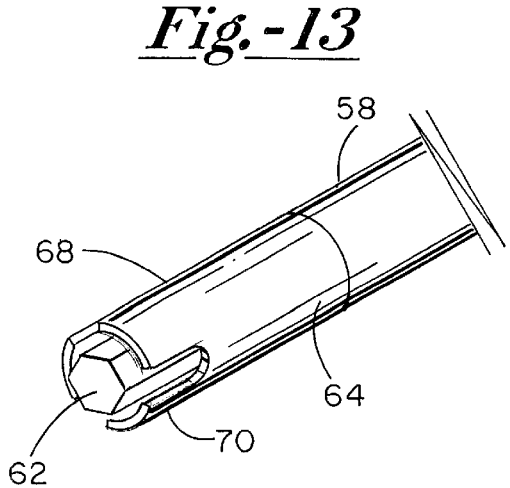
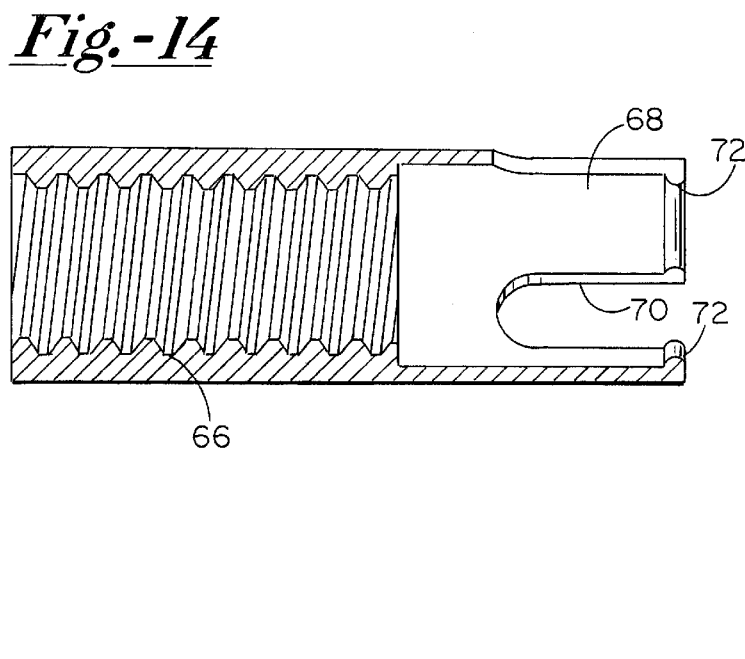
Fig.-12
Fig.-13
Fig.-14

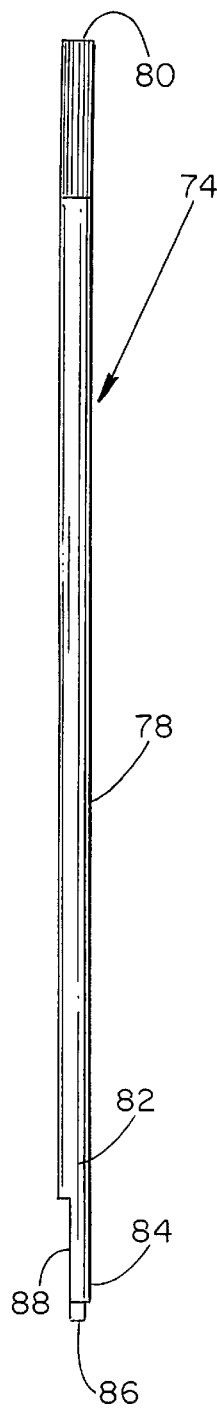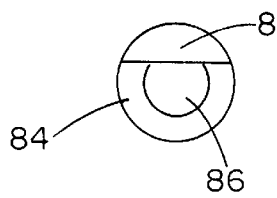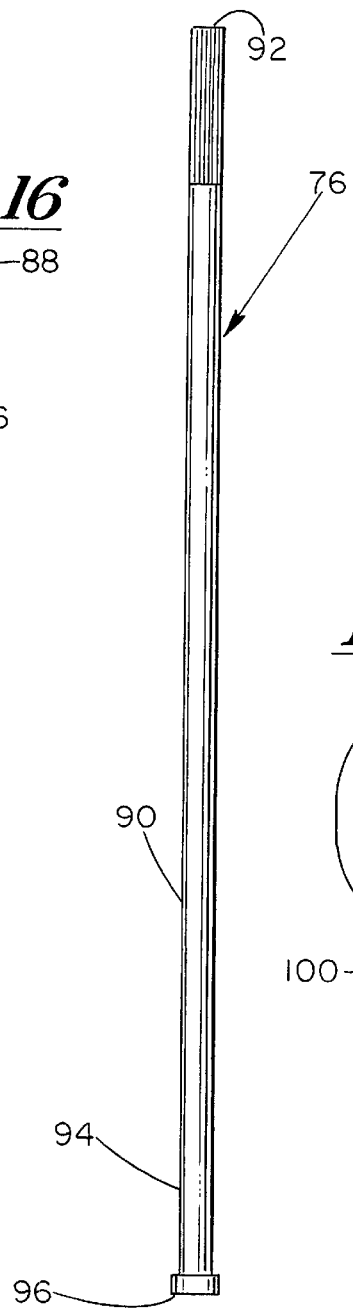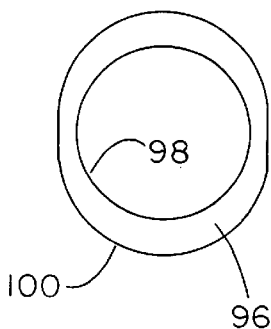

ANTERIOR CERVICAL PLATE AND FIXATION SYSTEM

This application claims the benefit of provisional application Ser. No. 60/085,962 entitled "Anterior Cervical Plate Fixation" filed May 19, 1998, and provisional application No. 60/105,976 entitled "Anterior Cervical Plate With Fastener Retaining Tabs" filed Oct. 28, 1998, which disclosures are incorporated herein.

BACKGROUND OF THE INVENTION

The present invention relates to cervical plates used for fusing cervical vertebrae in the treatment of spinal disorders, and more particularly to components for fastening such plates.

An increasingly accepted procedure for treating spinal disorders involves using substantially rigid plates to hold vertebrae in desired spatial relationships and orientations relative to each other. The upper cervical spine can be approached anteriorly or posteriorly, although anterior approaches are of more interest in connection with this invention. In either case, holes are drilled and tapped in at least two of the vertebrae, to receive screws or other fasteners used to secure the plate. The holes are accurately positioned with reference to openings formed through the cervical plate. In some cases the screws may be self-tapping. Typically the plate is curved about its longitudinal axis to facilitate contiguous surface engagement of the plates with the vertebrae. With the plate maintained against the vertebrae, the fasteners are secure within the holes. As a result, the plate maintains the attached vertebrae in a desired spacing and orientation with respect to each other.

One of the problems associated with this technique is the tendency of screws or other fasteners to gradually work loose after fixation. Slight shock or vibration of the vertebrae, due to walking, climbing stairs or more vigorous activity by the patient following treatment increases this tendency, jeopardizing the integrity of fixation. Moreover, as the fasteners work loose, the outward protrusion of the heads over other components of the fasteners can be a source of discomfort and present the risk of trauma to adjacent and surrounding soft tissue.

The curvature of cervical plates typically results in a convergence of fasteners that extend through spaced apart openings in the plate, particularly when each screw is perpendicular to the region of the plate surrounding it. Screws sufficiently short to avoid interfering with one another may not be long enough to assure a secure plate fixation. Further, the physician may encounter difficulties in positioning the plate if one of the vertebrae, due to a particular shape and orientation, cannot readily retain a perpendicularly inserted fastener.

There have been attempts to solve the above problems. For example, screws or other fasteners can be provided with somewhat rounded heads as shown in U.S. Pat. No. 5,324, 290 (Zdeblick). U.S. Pat. No. 5,261,910 (Warden, et al.) shows a nut with a rounded upper surface and a hexagonal recess. The nut has a conical portion that fits into a similarly shaped recess in a plate, thus to reduce the height at which the nut extends above the plate. U.S. Pat. No. 5,364,339 (Lowery, et al.) discloses an anterior cervical plate system in which the openings through the plate guide the screws in a non-perpendicular orientation that causes the screws to diverge, rather than converge, as they proceed into the particular cervical vertebra. The plate has a recess for limiting the degree of outward protrusion of the screw heads. After each pair of screws is fully inserted, a locking screw is threaded into the plate until its head encounters the heads of the bone screws.

While the above approaches yield favorable results in certain circumstances, there remains a need for greater flexibility in positioning and orienting the bone screws or fasteners, and for a simpler, more reliable means of counteracting the tendency of the bone screws to work loose after cervical plate fixation.

Therefore, it is an object of the present invention to provide a cervical plate and fixation system in which bone screws or other fasteners are more securely retained and less likely to work loose, without the need for auxiliary screws or other additional fixtures.

Another object is to provide a fastening system in which the heads of the fasteners are recessed within the cervical plate to minimize their protrusion beyond the plate.

A further object is to provide fastener receiving apertures in cervical plates that are shaped to allow a variety of angular orientations of the fasteners with respect to the plate.

Yet another object is to provide a system including cervical plates with locking features for retaining fastener heads, in combination with tools for conveniently manipulating the locking features to selectively retain or release the fasteners.

SUMMARY OF THE INVENTION

To achieve these and other objects, there is provided an appliance attachable to osseous or bony material within a body. The appliance includes a biocompatible structural member having an exterior surface including opposite first and second exterior surface regions. An interior surface region between the exterior surface regions defines an aperture through the structural member. A biocompatible fastener is provided, including an elongate longitudinal shank and a head larger in diameter than the shank. The shank is adapted for an insertion through the aperture and a penetration into osseous material to a depth sufficient to bring the first exterior surface region into a surface engagement with the osseous material while the head engages the interior surface region. Thus, the head tends to maintain the surface engagement to fix the structural member substantially integrally to the osseous material. A retaining element is permanently fixed to the structural member. The retaining element is moveable from an open position for allowing travel of the head into the aperture and against the interior surface region, to a closed position for maintaining the head against the interior surface region.

Preferably the retaining element is resilient and ductile, and moveable from the open position to the closed position by applying an external force above the elastic limit of the retaining element. The retaining element can be a tab supported in cantilevered fashion, or alternatively an elongate member attached at two opposite ends to the structural member. As another alternative, the retaining element can be elastic, normally (when not subject to external stresses) tending to assume to the closed position, and elastically deformable into the open position when subject to an external force.

The fastener head, when maintained in the aperture against the interior surface region, is advantageously contained between the first and second exterior surface regions, so that the head does not protrude outwardly beyond the plate or other structural member.

According to another aspect of the invention, the aperture is sized with respect to the shank to allow a pivoting of the fastener with respect to the structural member about at least one transverse axis. More preferably, the fastener is pivotable about all transverse axes passing through a given point in the first aperture, thereby defining a conical volume within which the fastener is selectively positionable.

The appliance preferably includes a second fastener substantially identical to the first fastener, and a second aperture through the structural member for receiving a head of the second fastener when a shank thereof is inserted through the second aperture. Then, for example, when the osseous material comprises two vertebrae, the structural member is positioned for extension of the first and second fasteners through their respective apertures into different ones of the vertebrae. Thus the fasteners cooperate with the structural member to support the vertebrae substantially integrally with respect to one another.

A system including the structural member and fasteners can further include tools for securing and removing the structural member, particularly in conjunction with resilient and ductile retaining elements. In particular, heads of the fasteners can include non-circular recesses, and a drive tool with a drive shaft can be provided, one end of the shaft having a non-circular profile corresponding to the profile of the recess. The fastener shanks, in this approach, are externally threaded, with a drive tool rotatable to turn the fasteners. The drive tool further can incorporate a sleeve coaxial with the drive shaft and incorporating flexure members to grip the fastener being turned by the drive tool.

Preferably, locking and releasing tools also are provided. The locking tool can include a shaft with a locking end positionable against the retaining element and movable to plastically deform the retaining element, moving the element into the closed position. The releasing tool has a releasing end positionable against the retaining element when the same is in the closed position. The releasing end is movable to force the retaining element into the open position to allow a withdrawal of the associated fastener.

Thus in accordance with the present invention, cervical plates and other structural members can be secured to vertebrae or other osseous material in a manner that more reliably prevents fasteners from working loose in response to shock or vibration. Resilient tabs or retaining members are moveable, through either plastic or elastic deformation, to open positions that allow insertion and removal of fasteners, and alternatively are positioned to prevent fasteners from working free of their respective apertures in the cervical plate or other structural members. The ability to select non-perpendicular angles at which the fasteners extend from the cervical plate permits relatively close positioning of fastener apertures without the risk of the fasteners interfering with one another, and more generally allows each fastener to be aligned for its most convenient or most secure angle of penetration into a vertebrae or other bony material.

IN THE DRAWINGS

For a further appreciation of the above and other features and advantages, reference is made to the following detailed description and to the drawings, in which:

FIG. 6 is a sectional view taken along the line 6—6 in FIG. 1;

FIG. 7 is a sectional view taken along the line 7—7 in FIG. 1;

FIG. 8 is an isometric view of one of the system fasteners;

FIG. 9 is a side view of the fastener;

FIG. 10 is a top view of the fastener;

FIG. 11 is a sectional view taken along the line 11—11 in FIG. 10;

FIG. 12 is a side view of a drive tool used to install the fasteners;

FIG. 13 is an isometric view of one end of the drive tool;

FIG. 14 is a side sectional view of a drive tool sleeve;

FIG. 15 is a side view of a locking tool shaft used to close the retaining feature;

FIG. 16 is an end view of the locking tool shaft;

FIG. 17 is a side view of a releasing tool shaft used to open the retaining feature;

FIG. 18 is an end view of the releasing tool shaft;

DETAILED DESCRIPTION OF THE PREFERRED EMBODIMENTS

Figure 1:
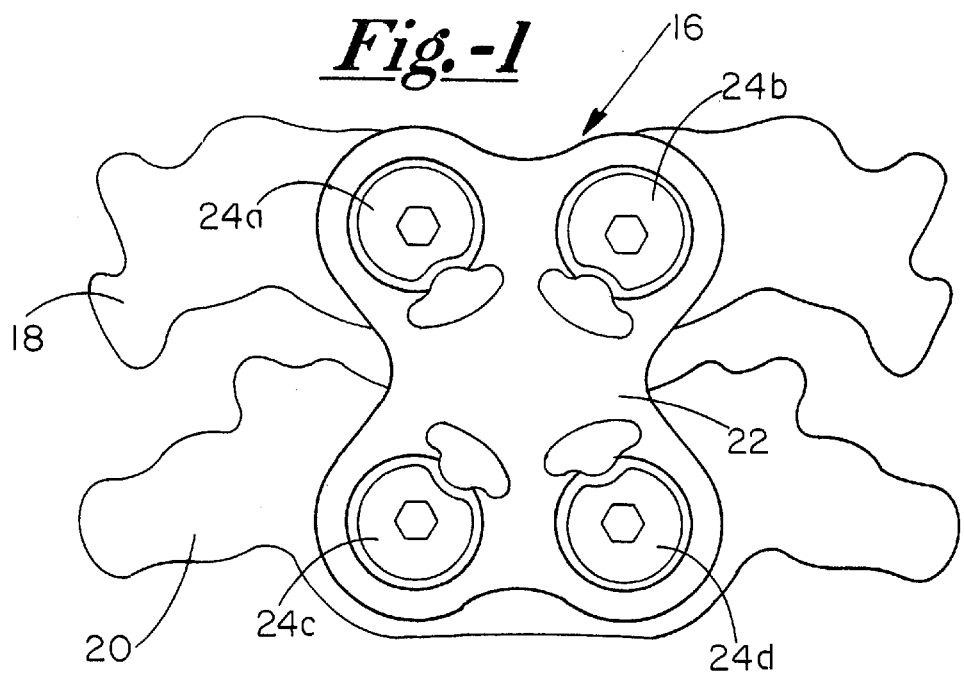
FIG. 1 is a schematic view of an anterior cervical plate and fixation system secured to two vertebrae in accordance with the present invention.

Turning now to the drawings, there is shown in FIG. 1 a cervical plate and fixation system 16 constructed in accordance with the present invention. System 16 is shown in connection with the upper cervical spine, secured to two vertebrae indicated at 18 and 20. The system is secured integrally to both of the vertebrae, and thus maintains the vertebrae integrally with respect to one another, in a desired orientation and at a desired spacing from one another as shown. System 16 includes a cervical plate 22 and four threaded fasteners or bone screws 24a–24d. Each of the fasteners extends through one of four apertures in the cervical plate, and further penetrates the osseous material (one of the vertebrae) to anchor the cervical plate.

The preferred material for plate 22 and fasteners 24 is titanium, which provides the requisite strength and resiliency for plate 22 to support the vertebrae in the manner indicated. Further, the titanium plate has sufficient ductility to permit curving the plate about a longitudinal axis (vertical in the figure) so that the cervical plate more readily conforms to the vertebrae. The ductility also plays a role in the use of retaining features that capture each fastener within its aperture, as will be explained.

Certain stainless steels are suitable as alternatives to titanium in the plate and fastener construction.

Figure 2:
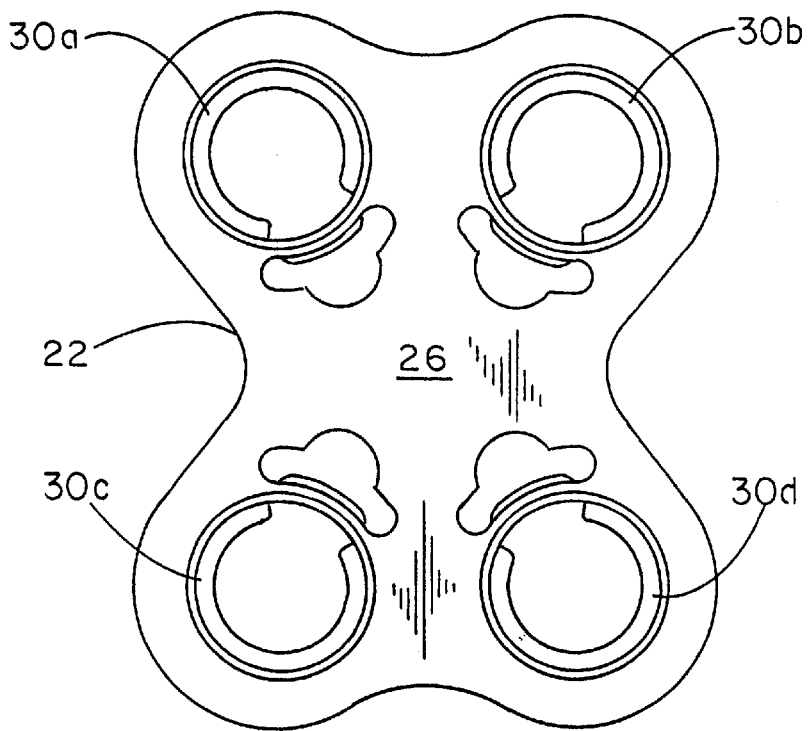
FIG. 2 is a top view of the cervical plate.
Figure 3:
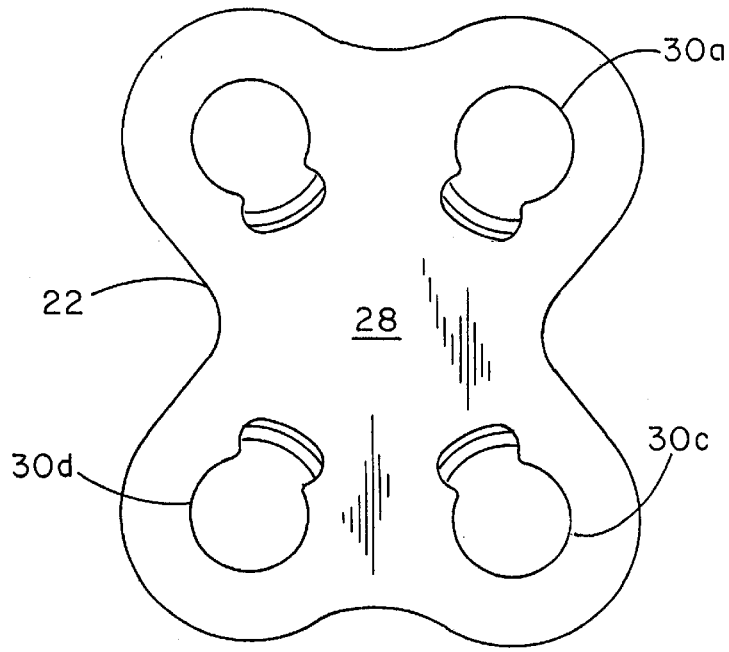
FIG. 3 is a bottom view of the cervical plate.

FIGS. 2 and 3 show cervical plate 22 apart from the fasteners, in top plan and bottom plan, respectively, and also show the plate in a flat configuration prior to its curvature to conform to the vertebrae. The plate has opposite anterior and posterior surfaces, indicated respectively at 26 and 28, that are parallel to one another and substantially planar before the plate is curved. Four pockets or apertures indicated at 30a–30d are formed through the cervical plate for receiving fasteners 24a–24d used to secure the plate to the osseous material of the vertebrae. The plate is symmetrical about longitudinal and transverse central axes, which are respectively vertical and horizontal as viewed in FIGS. 2 and 3.

Figure 4:
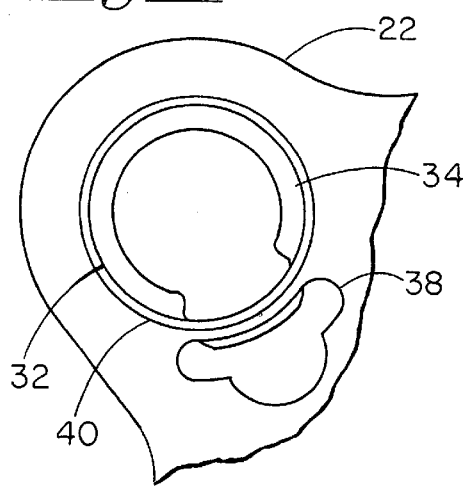
FIGS. 4 and 5 are enlarged partial top and bottom views, respectively.
Figure 5:
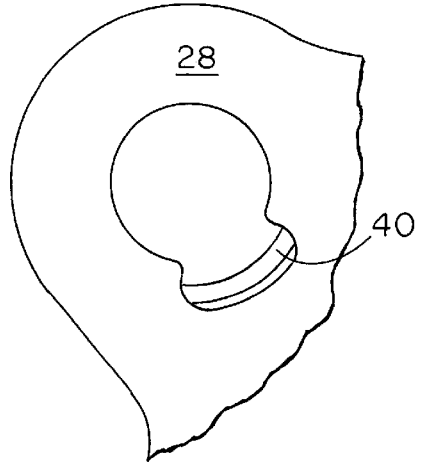

FIG. 4 illustrates aperture 30a and the surrounding portion of cervical plate 22 in greater detail. Because apertures 30b–30d are similar, only aperture 30a is described in detail. The aperture is defined by an interior wall of the plate that has three sections, an outer section 32, a spherical section 34 and an inner or posterior section 36 (FIG. 7). Outer section 32 is beveled at about a 45° angle relative to anterior surface 26. The spherical profile of section 34 conforms to a spherical profile of the associated fastener 24a. The utility of this arrangement is discussed below.

While outer section 32 is continuous about the aperture, spherical section 34 and posterior section 36 are not. More particularly, material is removed from plate 22, preferably by a laser machining process, not only to interrupt these latter sections but also to form a depression 38 open to the anterior side of the plate and extending approximately halfway through the plate thickness, as seen from FIG. 6. Further, a portion of the plate material between aperture 30a, beginning at a point inwardly of the anterior surface 26, is removed to leave a curved retaining feature 40. The retaining feature resembles a beam or bridge, attached at its opposite ends to the remainder of the cervical plate.

The preferred process for forming the retaining feature is laser cutting or laser machining, due to accuracy and the ability to control the depth of depression 38, e.g., to about 0.5 inches in a cervical plate having a thickness of about 0.9 inches.

FIGS. 8–11 show fastener 24a, which is substantially identical to the remaining fasteners. As seen in FIGS. 8 and 9, the fastener includes an elongate shank 42 with external threads 44 for securing the fastener within a vertebra or other bony material, thus to anchor plate 22. The fastener also has an enlarged head 46 with a spherical profile 48 sized to allow the head to nest within spherical section 34 of the aperture. At the outward end of the head is a projection 50 with an annular curved surface 52 to facilitate a gripping of the fastener with a tool described below.

As seen in FIG. 10, a hexagonal recess 54 is formed into the fastener head, to allow use of a tool with a hexagonal shaft to turn or drive the fastener. The head, projection and recess also are seen in FIG. 11.

FIG. 12 shows a drive tool 56 used to secure the fasteners by turning them into bony material, thus to secure the cervical plate. Tool 56 includes an elongate shaft 58 and a handle 60 fixed to the proximal end of the shaft. A distal end 62 of the shaft has a profile that is non-circular, in this case hexagonal, corresponding to recess 54 of the fastener. A sleeve 64 is removably mounted to shaft 58 near the distal end, positioned such that a portion of the shaft distal end projects beyond the sleeve.

As seen in FIG. 14, sleeve 64 is internally threaded at 66 and is removably mounted to shaft 58 by virtue of corresponding external threads (not shown) on the shaft. Three flexures or sleeve segments 68 project distally from the remainder of sleeve 58, separated from one another by gaps 70. At the end of each flexure is a nodule 72, as best seen in FIG. 14. When tool 56 is used to drive one of the fasteners, distal shaft end 62 is inserted into recess 54, while at the same time flexures 68 elastically bend sufficiently to position nodules 72 against curved surface 52 of projection 50. Thus, sleeve 64 holds the fastener firmly but releasably, to facilitate insertion and removal of the fastener.

The complete plate fixation system includes two further tools: a locking tool 74 and a releasing tool 76, used respectively to retain a fastener within its associated aperture and release the fastener from the aperture. FIG. 15 shows a locking tool shaft 78. The shaft is knurled at its proximal end as indicated at 80, for the later installation of a handle similar to handle 60. A distal end 82 of the shaft is shaped to provide two projections 84 and 86 that are substantially circular except for a flattened region 88.

Release tool 76 includes an elongate shaft 90 shown in FIG. 17, knurled at its proximal end 92 to accept a handle. A distal end 94 of the shaft supports a cuff 96 with a circular inside wall 98 surrounding the shaft, and a slightly elongated outer wall 100 presenting an oblong profile.

Use of system 16 to secure vertebrae 18 and 20 begins with forming (curving) and aligning cervical plate 22 to determine the proper locations for four openings to be drilled in the vertebrae to accommodate fasteners 24a–24d. The openings are then drilled and tapped. Due to the spherical profiles of the apertures and the fastener heads, the axial extension of each fastener need not be perpendicular to the cervical plate, but instead can be offset by pivoting the screw about an axis transverse to the longitudinal extension of the fastener. Thus, longer fasteners can be used for a more secure mounting, with the screws extended in directions to avoid their convergence or interference with one another.

Figure 19:
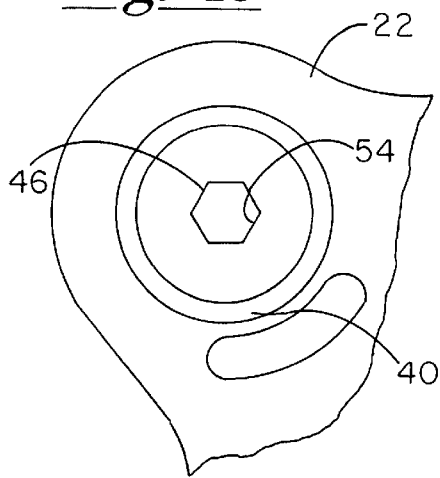
FIG. 19 is a top view similar to FIG. 2, further illustrating the fastener.
Figure 20:
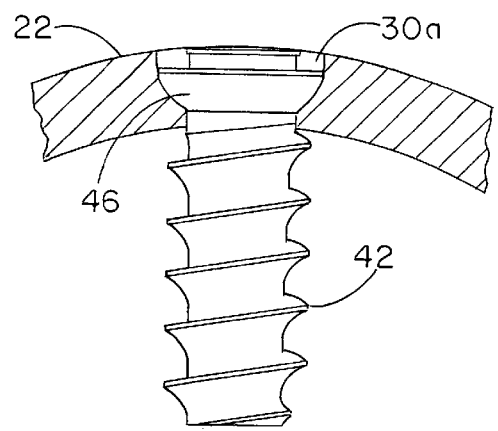
FIG. 20 is a sectional view taken along the line 20—20 in FIG. 19.

After the openings are drilled and tapped, cervical plate 22 is placed with posterior surface 28 in contact with the vertebrae. Fasteners 24a–24d are secured within their respective apertures 30a–30d, turned inwardly or in the posterior direction by using drive tool 56. Each of the bone screws or fasteners is turned inwardly, causing shank 42 to penetrate the osseous material of the vertebra to a depth sufficient to (1) bring spherical surface 48 of head 46 into engagement with spherical section 34 of the aperture, and (2) bring posterior surface 28 into contiguous engagement with the bony material. Thus, each fastener becomes nested within its associated aperture while urging the cervical plate against the bony material, as seen in FIG. 19 for fastener 24a. At this point head 46 and projection 50 are recessed within aperture 30, as best seen in FIG. 20.

At this stage, retaining feature 40 is plastically deformed to move a medial region 102 radially inwardly, to a closed position in which the retaining member overlies head 46 of the fastener. Retaining feature 40, when in the closed position, engages head 46 to prevent any substantial retraction or movement of fastener 24 in the anterior direction, substantially maintaining head 46 against section 34 of the aperture, which in turn maintains posterior surface 28 of the plate against the bony material. This overcomes any tendency in fastener 24 to work loose when the fastener and plate are subject to shock, vibration or other disturbance.

Figure 21:
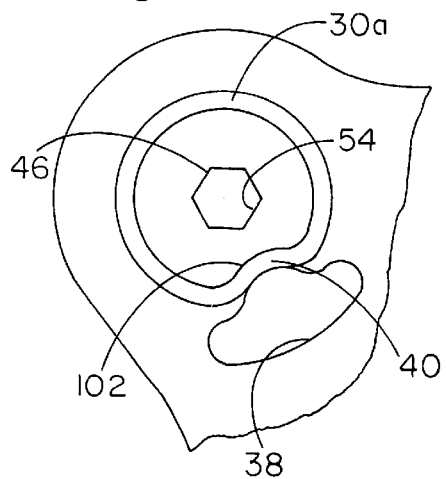
FIG. 21 is a top view similar to FIG. 19, illustrating a retaining feature in the closed position.
Figure 22:
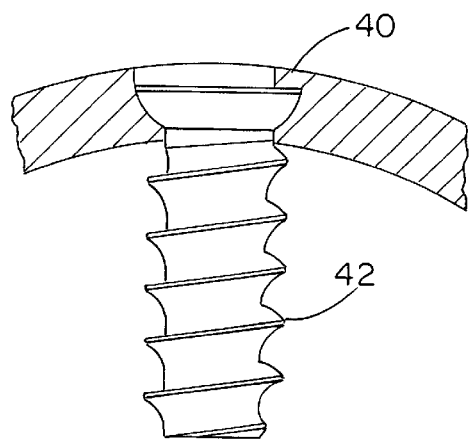
FIG. 22 is a sectional view taken along the line 22—22 in FIG. 21.

Tool 74 is used to close or lock the retaining feature. In particular, projections 84 and 86 of the shaft are inserted into depression 38 when retaining feature 40 is in the open position shown in FIG. 19, with a substantial portion of the shaft in a rounded sector 104 of the depression and flat region 88 facing feature 40. At this point shaft 78 is rotated, bringing wider portions of the projections into contact with the retaining feature, until the force applied to the feature exceeds its elastic limit and bends the feature to the closed position shown in FIG. 21. Again, titanium is the preferred material, providing a requisite ductility that enables retaining feature 40 to be plastically deformed as described, yet retain the degree of strength required to prevent retraction of the fastener. A slight force in the posterior direction is sufficient to retain the fastener.

It may become either necessary or desirable to inspect a previously installed cervical plate, or to reposition the plate, in either case requiring its removal. To this end, release tool 76 is inserted by its distal end into aperture 30, with cuff 96 oriented angularly so that the narrow-diameter portion is adjacent the closed retaining feature. From this position, shaft 90 is rotated, rotating the cuff to progressively present larger cuff diameters to the retaining feature. This eventually applies a force that exceeds the elastic limit of the feature, once again plastically deforming the feature to move it to the open position. This provides sufficient clearance for head 46 to pass through the aperture in the anterior direction, and also enables the insertion of drive tool 56 into the head to retract the fastener.

Figure 23:
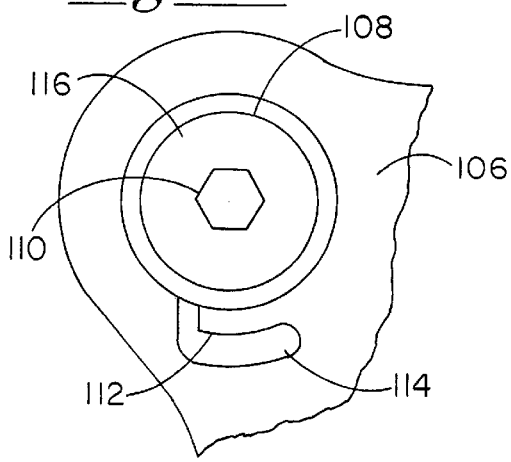
FIG. 23 is a partial top view of an alternative embodiment cervical plate.

FIG. 23 is a partial view of an anterior cervical plate 106 formed according to an alternative embodiment of the present invention. Plate 106 includes four apertures or pockets, one of which is shown at 108. A fastener 110, which can be substantially identical to fasteners 24, is nested within pocket 108. In connection with each pocket, material is removed by laser cutting or otherwise to form a tab 112 extended from the cervical plate in cantilevered fashion. In this figure, tab 112 is shown in the open position.

Figure 24:
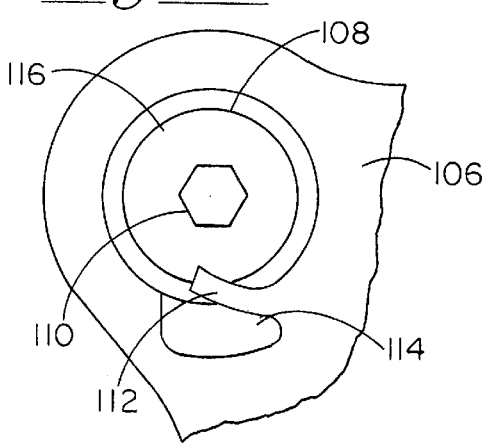
FIG. 24 is a top view similar to FIG. 23, showing a retaining tab of the plate in a closed position.

Cervical plate 106 is secured in much the same manner as described above for cervical plate 22. With tab 112 open, a locking tool such as tool 74 is inserted into a depression or cut-out 114, then rotated to bend tab 112 so that the tab overlies a portion of a fastener head 116 as seen in FIG. 24. Again, the deformation is plastic, so that the tab tends to remain in the closed position to maintain the fastener head within pocket 108.

In alternative embodiments, features like feature 40 and tab 112 can be resilient and less ductile, and normally (when not subject to external stress) in the closed position. A tool is used to elastically deform the tab or other feature to the open position, if it is necessary to retract the fastener.

Figure 25:
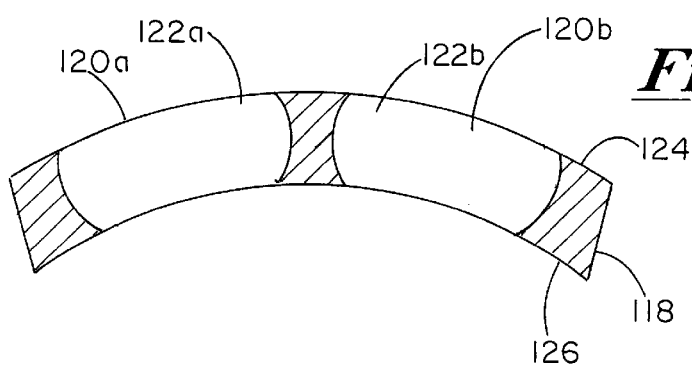
FIG. 25 is a sectional view of a further alternative embodiment cervical plate.

FIG. 25 is a sectional view of an anterior cervical plate 118 formed according to a further alternative embodiment of the invention. Two transversely spaced apart pockets 120a and 120b are illustrated, defined by spherical interior walls 122a and 122b, respectively. The center of each sphere is inside its associated pocket or aperture, i.e., between an anterior surface 124 and the posterior surface 126 of plate 118. Thus, each pocket includes a constriction 128 near the posterior surface, and a retaining feature in the form of a locking rim 130 near the anterior surface.

Figure 26:
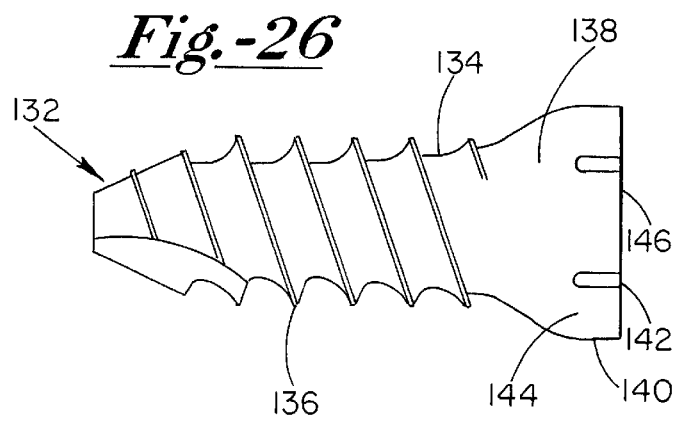
FIG. 26 is a side view of an alternative embodiment fastener used with the plate in FIG. 25.

FIG. 26 is a side elevation of an alternative embodiment bone screw or fastener 132. The screw includes an elongate shank 134 with exterior threads 136 for securing the screw within vertebra or other bony matter. The screw further has an enlarged head 138 with a spherical profile, as indicated at 140.

Figure 27:
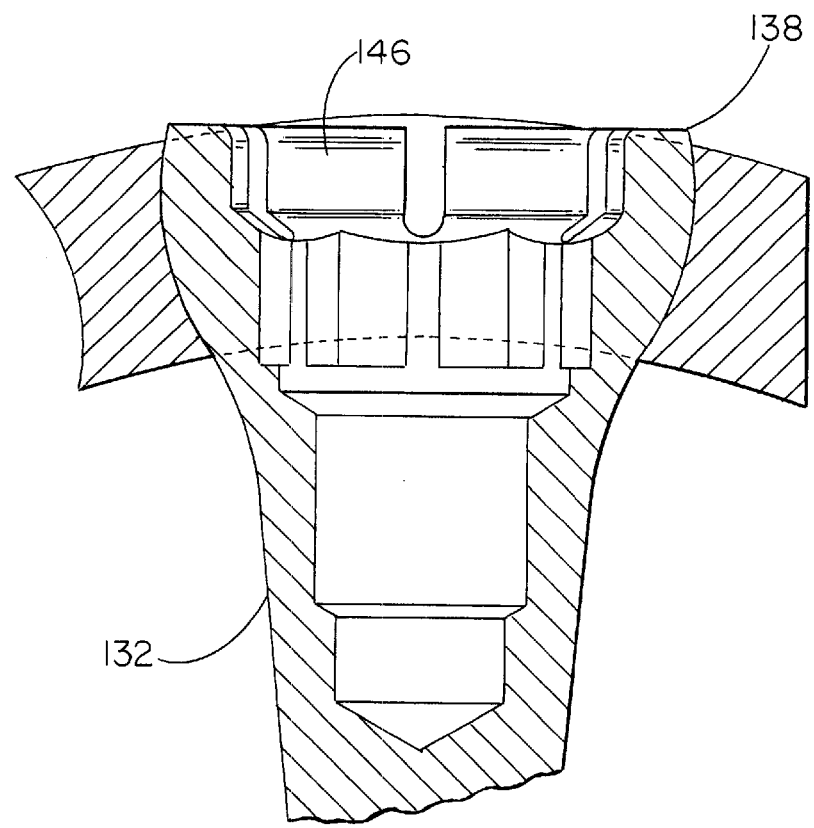
FIG. 27 is a sectional view showing the fastener installed within the plate.

FIG. 27 shows fastener 132 with head 138 secured within pocket 120a. Fastener 132, like fasteners 24 and 110, incorporates a hexagonal or other non-circular recess for use with a similarly profiled drive tool. Further, six slots 142 are formed in a peripheral wall 144 of head 138, to divide the peripheral wall into six arcuit wall segments 146. These slots, each open to the anterior end of the fastener, extend in the posterior direction beyond a transverse plane corresponding to the sphere diameter, i.e., the maximum diameter of head 138. This facilitates an elastic deformation, in particular a radially inward bending of wall segments 146, to reduce the diameter of head 138 sufficiently to allow posterior travel of the head past locking rim 130, to achieve a capture of the head within pocket 120. Once the maximum-diameter portion of the head has traveled past the locking rim, wall segments 146 return toward their relaxed state, effectively enlarging the head toward its original configuration so that the head remains captured within the pocket or aperture. Further, the respective spherical surfaces of the head and the pocket are maintained against one another, as seen in FIG. 27. In further alternative embodiments the locking rim rather than the head is elastically deformable to effect head capture.

Figure 28:
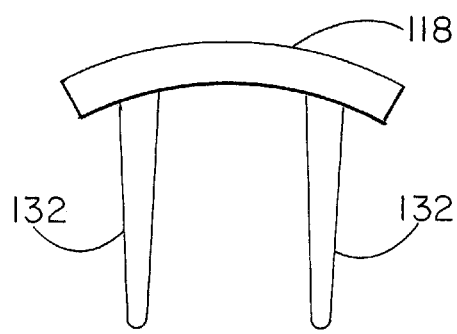
FIGS. 28 and 29 schematically illustrate alternative orientations of the fasteners with respect to the plate.
Figure 29:
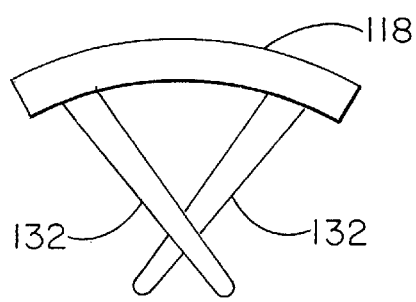

Bone screw or fastener 132 is shown with its longitudinal extension substantially perpendicular to cervical plate 118. However, it is readily apparent that the head can be pivoted about any number of transverse axes (transverse with respect to the longitudinal screw extension) so that the fastener can assume a variety of non-perpendicular orientations relative to the plate. As a result, adjacent fasteners 132 can be oriented in a diverging fashion, parallel as shown in FIG. 28, a converging but off-set fashion as in FIG. 29, or in a variety of other orientations, given the degrees of freedom for movement of each fastener head within its associated pocket. In this manner, the fastener orientations can be selected to improve or maximize holding strength, or to minimize the difficulty of drilling and tapping the bone screw holes and later installing the bone screws. All embodiments can incorporate this feature.

Thus, in accordance with the present invention, structural members such as cervical plates are secured to vertebrae and other bony material in a manner that substantially prevents the fasteners from working loose when subject to vibration. Retaining features, provided near each pocket or aperture that receives a fastener, are moveable between open and closed positions, either by elastic or plastic deformation. A further improvement resides in the ability to orient fasteners at a variety of non-perpendicular angles with respect to the cervical plate, which allows a relatively close spacing of fasteners without the risk of fasteners interfering with one another.

What is claimed is:

1. An appliance attachable to osseous material within a body, including:

a biocompatible structural member having an exterior surface including opposite first and second exterior surface regions, and an interior surface region between said exterior surface regions defining a first aperture through the structural member;

a biocompatible first fastener including an elongate longitudinal shank and a head larger in diameter than the shank, said shank adapted for a insertion through the first aperture and a penetration into osseous material to a depth sufficient to bring the first exterior surface region into a surface engagement with the osseous material while the head engages the interior surface region and thereby tends to maintain said surface engagement to fix the structural member substantially integrally to the osseous material; and a first retaining element permanently fixed to the structural member and movable from an open position for allowing travel of the head into the first aperture and against the interior surface region, to a closed position for maintaining the head against the interior surface region.

2. The appliance of claim 1 wherein:
the first retaining element is resilient and ductile, and movable from the open position to the closed position by applying an external force above an elastic limit thereof.

3. The appliance of claim 2 wherein:
said retaining element comprises a tab supported by the structural member and extending therefrom in cantilevered fashion.

4. The appliance of claim 2 wherein:
the retaining element comprises an elongate member attached at two opposite ends to the structural member.

5. The appliance of claim 1 wherein:
said first retaining element is elastic, normally tending to assume the closed position, and elastically deformable into the open position when subject to an external force.

6. The appliance of claim 1 wherein:
the first exterior surface region and the second exterior surface region are substantially parallel to one another.

7. The appliance of claim 6 wherein:
the head, when maintained in the first aperture against the interior surface region, is substantially contained between the first and second exterior surface regions.

8. The appliance of claim 1 wherein:
the shank is externally threaded, the head incorporates a non-circular recess for receiving a drive tool used to turn the fastener.

9. The appliance of claim 1 wherein:
the aperture is sized with respect to the shank to allow a pivoting of the first fastener with respect to the structural member about at least one transverse axis disposed between the first and second exterior surface regions when the head is in the aperture.

10. The appliance of claim 9 wherein:
the first fastener is pivotable about all transverse axes passing through a given point between the first and second exterior surface regions, thereby defining a conical volume within which the first fastener is selectively positionable.

11. The appliance of claim 10 wherein:
said interior surface region includes a spherical segment, and said head has a spherical surface portion in contact with the spherical segment.

12. The appliance of claim 1 further including:
a second fastener substantially identical to the first fastener, and a second aperture formed though the structural member for receiving a head of the second fastener when a shank thereof is inserted through the second aperture.

13. The appliance of claim 12 wherein:
the first and second apertures are disposed near opposite ends of the structural member, the osseous material comprises two vertebrae, and wherein the structural member is positionable with respect to the vertebrae such that the first and second fasteners are extendible through the first and second apertures respectively and into different ones of the vertebrae, and cooperate with the structural member to support the vertebrae substantially integrally with respect to one another.

14. The appliance of claim 1 wherein:
said biocompatible structural member is unitary, and the first retaining element is formed as part of the unitary biocompatible structural member.

15. The appliance of claim 1 wherein:
said first retaining element further is movable from the closed position to the open position to allow a removal of the head from the first aperture, thus to allow a withdrawal of the first fastener from the osseous material and the structural member.

16. An apparatus for fixing a body insertable member to bony material, including:
a biocompatible structural member having an exterior surface that includes a first surface region adapted for surface engagement with a bony material when the structural member is secured to the bony material, and a second surface region opposite the first surface region;
a first fastener comprising an elongate shank extending in a longitudinal direction and having a transverse shank diameter, and further including a head having a transverse head dimension larger than the shank diameter;
an interior wall defining a first aperture formed through the structural member, including a first constriction proximate the first surface region selectively sized with respect to the first fastener to allow passage of the shank through the aperture and first constriction while preventing such passage of the head to maintain the head within the aperture, said first constriction further being of sufficient size to allow a pivoting of the first fastener with respect to the structural member about at least one transverse axis, thereby to allow the selection of a penetration angle at which the shank is inserted into the bony material to secure the structural member; and
a head retaining feature integral with the structural member, disposed near the first aperture and proximate the second surface region, and adapted to cooperate with the first constriction to maintain the head in the first aperture;
wherein at least one of said head and said head retaining feature is elastically deformable to allow travel of the head past the head retaining feature into the first aperture.

17. The apparatus of claim 16 wherein:
the head and the constriction are shaped to allow said pivoting about all of the transverse axes passing through a given point within the aperture.

18. The apparatus of claim 17 wherein:
the first fastener is pivotable throughout a conical volume centered on an axis substantially perpendicular to the first surface region near the aperture and intersecting said point.

19. The apparatus of claim 16 wherein:
the interior wall and the head have respective spherical sections engaged with one another when the head is in the aperture.

20. The apparatus of claim 19 wherein:
the interior wall extends between the first and second surface regions.

21. The apparatus of claim 20 wherein:
the spherical sections of the head and the interior wall are substantially concentric, and the center of the spherical sections is disposed between the first and second surface regions, whereby the interior wall further defines the head retaining feature.

22. The apparatus of claim 21 wherein:
the head is elastically deformable to allow the head to travel past the head retaining feature into the aperture.

23. The apparatus of claim 16 wherein:
the head retaining feature maintains the head at least proximate the constriction to prevent withdrawal of the fastener from the aperture.

24. The apparatus of claim 23 wherein:
the head retaining feature comprises a retaining element fixed to the structural member, movable from an open position for allowing travel of the head into the aperture and against the constriction, to a closed position for so maintaining the head.

25. The apparatus of claim 24 wherein:
the retaining element is resilient and ductile, and movable from the open position to the closed position by applying an external force above an elastic limit thereof.

26. The apparatus of claim 24 wherein:
the retaining element is elastic, normally tending to assume the closed position and elastically deformable into the open position when subject to an external force.

27. A bone plate and fixation system, including:
a biocompatible bone plate having an exterior surface including a bone contact surface region adapted for surface engagement with vertebrae;
first and second spaced apart apertures formed through the bone plate, each of the apertures including a constriction proximate the bone contact surface region;
first and second fasteners, each fastener including an elongate shank extending in a longitudinal direction and having a transverse shank diameter, and further including a head having a transverse head dimension greater than the shank diameter;
wherein the constriction in each of the first and second apertures is selectively sized with respect to its associated fastener to allow a passage of the shank of the associated fastener through the aperture while engaging the head to prevent such passage of the head; and
first and second retaining elements permanently fixed to the structural member and associated with the first and second apertures, respectively, each retaining element being movable from an open position for allowing travel of the head of its associated fastener into its associated aperture and against the constriction thereof, to a closed position for maintaining the associated head substantially against the associated constriction.

28. The system of claim 27 wherein:
each of the retaining elements is resilient and ductile, movable from the open position to the closed position by applying an external force that exceeds an elastic limit of the retaining element.

29. The system of claim 28 wherein:
the retaining elements comprise tabs extending from the structural member in cantilevered fashion.

30. The system of claim 28 wherein:
each of the retaining elements comprises an elongate member attached at two opposite ends to the structural member.

31. The system of claim 27 wherein:
each of the retaining elements is elastic, normally tending to assume the closed position and elastically deformable into the open position when subject to an external force.

32. The system of claim 27 wherein:
the exterior surface of the bone plate further includes an outer surface region opposite the bone contact surface region, and the heads, when maintained in their respective apertures against their respective constrictions, are substantially contained between the bone contact surface region and the outer surface region.

33. The system of claim 27 wherein:
the shanks of the fasteners are externally threaded, and the respective heads incorporate non-circular recesses for receiving a drive tool used to turn the fasteners.

34. The system of claim 27 wherein:
the constrictions are of sufficient size to allow a pivoting of their respective fasteners with respect to the structural member, each about at least one transverse axis, thereby to allow the selection of respective penetration angles at which the shanks are inserted into the vertebrae to secure the structural member.

35. The system of claim 34 wherein:
each of the heads and their associated constrictions is shaped to allow said pivoting about all of the transverse axes passing through a given point within the associated aperture.

36. The system of claim 33 further including:
a fastener drive tool having a drive shaft, said shaft having an end region with a non-circular profile corresponding to said non-circular recess in the respective heads.

37. The system of claim 36 further including:
a sleeve substantially coaxial with and surrounding said end of the drive shaft.

38. The system of claim 27 wherein: the sleeve is removably attached to the drive shaft.

39. The system of claim 38 further including:
a plurality of flexure members at a distal end of the sleeve, for gripping one of the fasteners when said end of the drive shaft is received within its associated recess.

40. The system of claim 27 further including:
a locking tool including a shaft with a locking end positionable against the retaining element and movable to plastically deform the retaining element and thereby move the retaining element into the closed position.

41. The system of claim 27 further including:
a fastener releasing tool having a shaft with a releasing end positionable against the retaining element when the same is in the closed position, and movable to force the retaining element into the open position to allow a withdrawal of the associated fastener.

* * * * *